United States Patent [19]
Elazar et al.

[11] 3,945,250
[45] Mar. 23, 1976

[54] FLOW TRANSDUCERS

[75] Inventors: Shmuel Elazar, Camarillo; Charles A. Bierbaum, Port Hueneme, both of Calif.

[73] Assignee: Statham Instruments, Inc., Oxnard, Calif.

[22] Filed: Apr. 19, 1974

[21] Appl. No.: 462,345

[52] U.S. Cl. .................... 73/194 EM; 128/2.05 F
[51] Int. Cl.² ........................................ G01F 1/58
[58] Field of Search ........... 73/194 EM; 128/2.05 F

[56] References Cited
UNITED STATES PATENTS

| | | | |
|---|---|---|---|
| 3,309,924 | 3/1967 | Kolin et al. | 73/194 EM |
| 3,696,674 | 10/1972 | Spencer | 73/194 EM |
| 3,751,980 | 8/1973 | Fryer | 73/194 EM |

*Primary Examiner*—Charles A. Ruehl

[57] ABSTRACT

This invention relates to a flow velocity transducer particularly adapted to the determination of blood flow in blood vessels.

8 Claims, 6 Drawing Figures

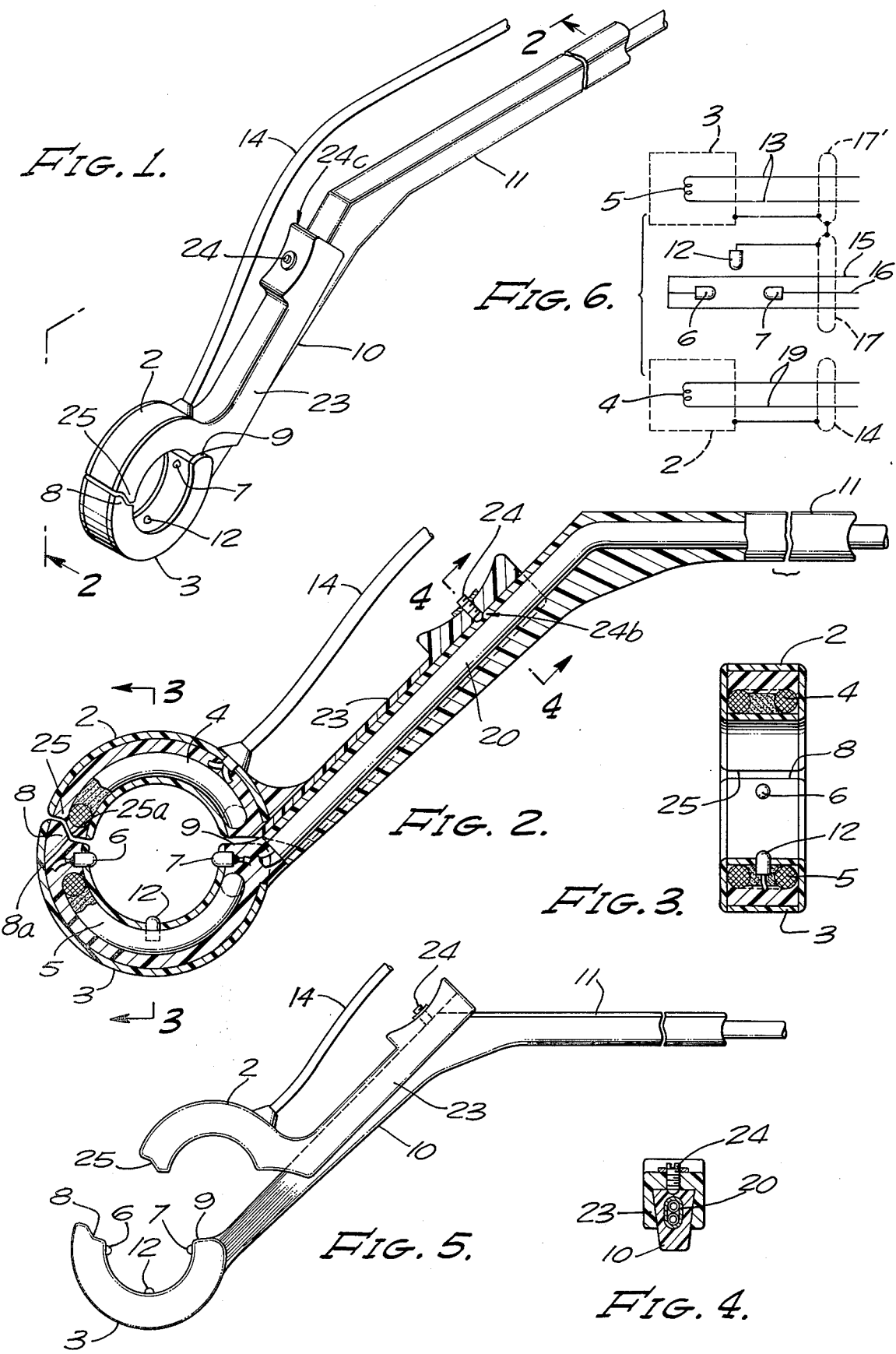

FLOW TRANSDUCERS

This invention relates to flow velocity transducers and in its presently preferred embodiment to blood flow meters.

BACKGROUND OF THE INVENTION

Blood flow probes based on the so-called Faraday principle are standard devices used to measure blood flow velocity through veins and arteries. In one form of these devices, they are in the form of lumens which may be placed about the vein or artery. The lumen contains electromagnetic coils and electrical terminals. The energizing of the coil generates a magnetic field and a potential is generated between suitably placed electrodes which is proportional to the volumetric rate of blood flow.

Reference may be had to Kolin U.S. Pat. No. 3,309,924; Westersten U.S. Pat. No. 3,316,762; and Hickman U.S. Pat. No. 3,580,071 for details of construction of such flow probes. See also "Single-Coil Coreless Electromagnetic Blood Flow Meters" by Kolin and Wisskaupt in IEEE Transaction on Bio-Medical Electronics, Vol. BME 10 No. 2, April 1963.

The prior art probes as illustrated by the above patents had a number of difficulties. In order to insert the artery or vein into the lumen, an opening is necessary. Two procedures for this purpose have been employed in the prior art. In one form (see Kolin U.S. Pat. No. 3,309,924), the lumen is split into two parts; and a hinge is provided at adjacent ends of the semicircular halves of the lumen, the other end being free. Another solution is to provide a window in the lumen through which the artery or vein may be passed and a shutter is used to close the window.

In the hinged form (see, for example, Kolin U.S. Pat. No. 3,309,924), there is a problem of holding the free ends of the lumen section in locked position to be sure they do not separate. The angle which may be subtended by the coils is limited by the space occupied by the hinge.

Another problem arises from the hazards of injury to the blood vessel by the closing of the hinged section about the blood vessel. Another hazard resides in the presence of the hinge which may cause injury or irritation to the surrounding tissues.

This type of lumen has been replaced by lumens in which a window is provided which may be closed by a plug as referred to above. This type has been used in two forms. In the above Kolin type, a single coil has been employed. The angle subtended by the coil limits the size of the opening. In order to provide a sufficient arcuate angle subtended by the coil and also pass the blood vessel, the internal diameter of the lumen must be made substantially greater than the opening at the window. For example, in the Kolin patent, the window is made somewhat less than 120°; and the coil subtends about 240°.

Kolin states (see U.S. Pat. No. 3,309,924) that, in the shutter types using two coils, each coil subtends approximately 60°. For example, in Hickman U.S. Pat. No. 3,580,071, the magnetic influences of two coils subtend approximately 180°.

The sensitivity of the lumen expressed as millivolts of signal output per unit of blood flow is related to the angle subtended by the magnetic coils so that the greater is the angle about the lumen encompassed by the coils the greater is the sensitivity. As a rough approximation, the sensitivity may be taken as proportional to the angle subtended by the coils, all other parameters being the same.

All of the above forms of the prior art devices have the disadvantage that the internal diameter of the lumen is greater than the opening at the window, so that either the blood vessel must be squeezed through the window or the lumen will be greater than the diameter of the blood vessels which will impair the functioning of the flow probe.

All of the forms described above have the disadvantage that it requires the use of both hands to manipulate the unit to open and close it.

Another form of probe with shutter-closed openings is the so-called handle probe in which the lumen is mounted on a handle which extends along a prolongation of a diametric plane of the cylindrical lumen. The shutter is mounted on a slide which may be moved away from the lumen to open the window. As in the previous shutter-type lumens, the shutter is substantially less than 180°; and the coils are all mounted in the portion of the lumen attached to the handle. In this form, the opening is of the same angular order and the magnetic field is of the same nature as is described above for the other forms of shutter lumens.

STATEMENT OF THE INVENTION

It is an object of our invention to provide a flow probe transducer of the Faraday type which may be opened to install the blood vessel in the lumen and which may be closed with the same hand.

It is another object of our invention to make the opening variable at the will of the operator and, if desired, substantiallly equal to the internal diameter of the lumen.

It is another object of our invention to provide a magnetic field generated by coils to an angular degree which is substantially in excess of that permissible by the prior art.

We form the cylindrical lumen in two parts. While we prefer to mount to an electromagnetic coil in each part, the coil may be positioned in one or the other of the lumen parts. We provide means for moving the parts relative to each other so as to provide a free space between the adjacent ends of the lumen parts. The direction of motion is in a longitudinal direction so that no hinge between the parts need be provided.

In our preferred embodiment, the parts are moved relative to each other so as to separate both ends of each part of the lumen. The direction of relative motion of the ends of the parts is at an acute angle to the plane of the ends of each of the parts when assembled.

In a preferred embodiment, the electrodes of the probe are mounted in one of the parts on a chordal plane of the cylindrical lumen part which may be a diametric plane. The longitudinal direction of motion of the other part may be at an acute angle to the aforementioned plane. In order to accommodate the electrodes, the part containing them may be made to cover a greater angle than the complementary part of the lumen.

In our preferred embodiment, we mount the part containing the electrodes on a handle which is attached to the lumen end at an acute angle to the aforesaid plane and the other part is mounted on a slide on said handle. The angular dimensions and the angular direction of the longitudinal motion are such that the free end of the part mounted on the slide will not interfere with the other part. In such configuration, the slide mounted part may be moved at such angle so that its free end may be moved away from the free end of the other part so that the distance between the free ends may be equal to or less than or greater than the internal diameter of the assembled lumen. The opening is at the will of the operator. In the preferred embodiment, one part of the lumen may be removed completely from the other part of the lumen.

This design permits the coils to subtend substantially the entire 360° of the lumen, limited only by the structural necessity of enclosing the coils.

In our preferred embodiment due to the requirement of the placement of the electrodes relative to the magnetic field, we prefer to limit the angular extension of the coils so that there is sufficient angular space to place the electrodes. The angle subtended by both coils because of structural necessity and space for the electrodes may be, for example, up to about 340°. This is a much greater angle than was possible in the prior art.

DETAILED DESCRIPTION

This invention will be described in connection with the drawings which illustrate our presumably preferred embodiment.

FIG. 1 is a perspective view of our flow probe shown in closed position.

FIG. 2 is a section taken along broken line 2—2 of FIG. 1.

FIG. 3 is a section on line 3—3 of FIG. 2.

FIG. 4 is a section on line 4—4 of FIG. 2.

FIG. 5 is a perspective view of the probe in open position.

FIG. 6 is a schematic view of the circuitry.

The lumen is formed of two arcuate parts 2 and 3; an arcuate bent coil 4 is encapsulated in part 2, and a bent coil 5 is encapsulated in part 3. The electrodes 6 and 7 are mounted in the conventional relation to the magnetic field for a Faraday type flow probe. For this purpose, they are mounted within the body of the part 3 below the free end 8 and the end 9 of the part 3. The end 9 is connected to or formed integrally with a handle 10 which extends at an angle to the chord connecting electrodes 6 and 7. We prefer to employ a 45° angle. For convenience of holding the probe, the handle is joined to a handle part 11 which extends at an obtuse angle to the handle part 10.

The electrical leads 13 connected to the coil 5 are encased by cable sheath 17' which passes through tube 20 embedded in handle 10 and 11. A ground electrode 12 may be provided in the part 3 or an external ground connection may be utilized. The leads 15 and 16 connected to the electrodes 6 and 7 are encased by a cable sheath 17 which also passes through tube 20 for connection to suitable readout. The ground electrode is connected to cable sheath 17 and 17'. The leads 19 connected to the coil 4 are encased by cable sheath 14.

The lumen part 2 is mounted on the slide 23 shaped to form a wedge dovetail with the handle 10 so that it may slide up and down the handle 10 and may be entirely withdrawn from the handle. The slide may be held in a selected position on the handle 10 by the screw 24 which fits in the recess 24B when the lumen is assembled. The screw is adjusted to permit the slide to move. When the screw reaches the recess, it "jumps" into the recess. The screw may be made of flexible material, such as nylon. The screw in the recess acts to lock the lumen in position.

As will be seen by sliding the part 23 up the handle, the part moves so as to separate the free ends 8 and 25, providing an opening which is in direction substantially parallel to the handle 10 and at an acute angle to the line connecting 6 and 7. The size of the opening is dependent on how far up the handle the slide is moved. The slide and lumen part 2 may be removed completely from the handle. This permits the lumen part 3 to be maneuvered into position under an artery or other vessel. The slide may then be positioned on the handle and slid into position as shown in FIG. 2.

The free ends of the lumen halves are formed with parallel ends 8a and 25a forming an interface between the lumen halves which are interference surfaces. These are entered at an acute angle to the horizontal diameter of the lumen. The pulsation of the artery creates a pressure against the internal surface of the lumen. The arrangement of the surfaces does not permit any substantial relative displacement of the lumen parts and eliminates electrical artifacts which would otherwise occur. The fit of 8a with respect of 25a may be as close as is practically accomplished in manufacture.

The device has particular utility where it is used as a periarterial probe. The slide may be moved to open the lumen and may be held in position with one hand. The blood vessel may be inserted without constricting the blood vessel unlike a probe of like diameter which is of the shutter type.

We claim:

1. A blood flow transducer comprising a lumen section, said lumen section being split into a pair of arcuate lumen parts, an arcuate electromagnetic coil mounted in said lumen section, a pair of electrodes mounted in said lumen section, and mounting means for said lumen parts to enable selective rectilinear relative displacement therebetween, whereby said parts may be separated to provide a gap between adjacent edges thereof and moved towards each other to close said gap.

2. The flow transducer of claim 1 in which said electrodes are mounted on opposite sides of one only of said lumen parts and said other lumen part is mounted by said mounting means for movement at an angle to a line connecting said electrodes.

3. The flow transducer of claim 1 in which said arcuate electromagnetic coil is composed of a pair of sections, one section positioned in each lumen part.

4. The flow transducer of claim 3 in which said electrodes are mounted on opposite sides of one only of said lumen parts and said other lumen part is mounted by said mounting means for movement at an angle to a line connecting said electrodes.

5. A blood flow transducer comprising a lumen section, said lumen section being split into a pair of arcuate lumen parts, each part having a pair of free ends, an arcuate electromagnetic coil mounted in said lumen section, a pair of electrodes mounted in said lumen section, and mounting means for said lumen parts to enable selective separation of both ends of one lumen part from both ends of the other lumen part, whereby said parts may be separated to provide a gap between adjacent ends thereof and moved towards each other to close said gap.

6. The flow transducer of claim 5 in which said electrodes are mounted on opposite sides of one only of said lumen parts and said other lumen part is mounted by said mounting means for movement at an angle to a line connecting said electrodes.

7. The flow transducer of claim 5 in which said arcuate electromagnetic coil is composed of a pair of sections, one section positioned in each lumen part.

8. The flow transducer of claim 7 in which said electrodes are mounted on opposite sides of one only of said lumen parts and said other lumen part is mounted by said mounting means for movement at an angle to a line connecting said electrodes.

* * * * *